(12) United States Patent
Kubata et al.

(10) Patent No.: US 7,566,465 B2
(45) Date of Patent: Jul. 28, 2009

(54) ARTEMISININS IN THE CLINICAL AND VETERINARY MANAGEMENT OF KINETOPLASTID INFECTIONS

(75) Inventors: Bruno K. Kubata, Nairobi (KE); Samuel K. Martin, Burtonsville, MD (US); Wilbur K. Milhous, Germantown, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/644,494

(22) Filed: Dec. 21, 2006
(Under 37 CFR 1.47)

(65) Prior Publication Data

US 2008/0152729 A1    Jun. 26, 2008

(51) Int. Cl.
*A61K 36/282* (2006.01)
(52) U.S. Cl. ...................................... 424/740
(58) Field of Classification Search ........................ None
See application file for complete search history.

(56) References Cited

U.S. PATENT DOCUMENTS 6,461,603 B2 * 10/2002 Bentley et al. ............ 424/78.19
2003/0171424 A1 * 9/2003 Lin et al. .................... 514/452
2004/0067875 A1 * 4/2004 Lai et al. ........................ 514/6
2005/0240034 A1 * 10/2005 Avery et al. ................. 549/349
2007/0032460 A1 * 2/2007 Stella et al. .................. 514/154

FOREIGN PATENT DOCUMENTS

WO     WO 03/095444     11/2003
WO     WO 2006/097472    9/2006

OTHER PUBLICATIONS

Yang D M et al, Effects of Qinghaosu (artimisinin) and its derivatives on Experimental cutaneous leishmaniasis, Parasitology, Cambridge Univ. Press, London, GB, vol. 106, No. 1, 1993, p. 7-11.
Dardonville C, Recent advances in antitrypanosomal chemotherapy, Patent literature 2002-2004, Exper Opinion on Therapeutic Patents 2005, United Kingdom, vol. 15, No. 9, 2005, pp. 1241-1257.
Mishina Y V et al: Artemisinins inhibit trypanosoma brucei rhodesiense in vitro growth, Antimicrobial Agents and Chemotherapy 2007, United States, vol. 51, No. 5, 2007, pp. 1852-1854.

* cited by examiner

*Primary Examiner*—Christopher R. Tate
*Assistant Examiner*—Deborah A. Davis
(74) *Attorney, Agent, or Firm*—Elizabeth Arwine

(57) ABSTRACT

The invention relates to the treatment of kintoplastid infections by administering a pharmaceutical composition containing an extract from the plant *Artemisia annua*. The invention also relates to isolated, semi-synthetic and synthetic artemisinins that show improved efficacy in treating kinetoplastid infections. This invention also relates to a method of treating kintoplastid infections with artelinic acid and artemisinins and where Artelinic acid is administered orally.

6 Claims, 7 Drawing Sheets melarsoprol difluoromethyl ornithine / DFMO

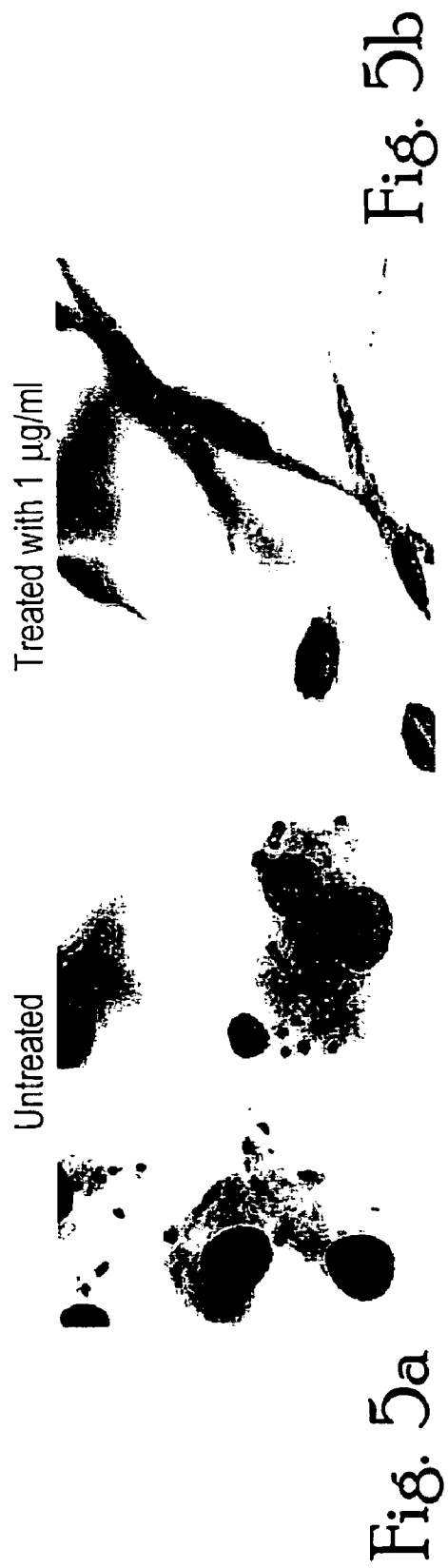
Fig. 5a  Untreated
Fig. 5b  Treated with 1 μg/ml
Fig. 5c  Treated with 10 μg/ml
Fig. 5d  Treated with 100 μg/ml

ARTEMISININS IN THE CLINICAL AND VETERINARY MANAGEMENT OF KINETOPLASTID INFECTIONS

GOVERNMENT INTEREST

The invention described herein may be manufactured, used and licensed by or for the U.S. Government.

BACKGROUND OF THE INVENTION

1. Field of the Invention

This invention relates to methods of treating and managing kinetoplastid infections by administering artemisimins and artelinic acid.

2. Brief Description of Related Art

Trypanosomiasis is a re-emerging [1-3] tropical infectious disease that poses a real challenge to public health countermeasures. According to the World Health Organization (WHO) [4], about 36 sub-Saharan countries in West, Central, and East Africa and some 22 Latin countries in Central and South America delimit its geographic prevalence zone, thus, leading to the establishment of two distinct manifestations of the disease: African trypanosomiasis and American trypanosomiasis.

*Trypanosoma* species pathogenic to human beings and domestic animals in Africa, cause one of the world's most neglected tropical infections—African trypanosomiasis [3]. Nearly eliminated in the 1960s, African trypanosomiasis has been making an alarming comeback due to civil wars, population displacements, and the collapse of public health systems mainly due to political instability (www.accessmed-msf.org/documents/ssfactsheet.pdf) [1]. Human African trypanosomiasis (HAT) threatens 60 million [1,3-6] men, women, and children among, principally, the rural populations, but actually even the citadin populations, in countries of high endemicity such as Angola, southern Sudan, the Democratic Republic of Congo, and northern Uganda. The incidence rate in HAT is estimated between 300,000-500,000 cases annually [3-6] and only 3 to 4 million people at risk are under regular medical surveillance (http://www.who.int/inffs/en/fact259.htlm). In animal African trypanosomiasis (AAT), the infection threatens about 50 million head of cattle with an estimation of 3 million deaths per year in livestock (http://www.fao.org/ag/againfo/programmes/en/paat/disease.htlm).

American trypanosomiasis ("Chagas disease") occurs mainly in countries such as Brazil, Chile, Mexico, Uruguay, Paraguay, Bolivia, and Argentina [10, 11]. Over 13 million persons in the Southern American region are at risk of infection and the annual incidence rates of the disease reaches 200,000 cases in 15 endemic countries [10]. The bloodstream protozoan *Trypanosoma cruzi* [10-12] is the etiologic agent of Chagas disease.

Host-to-host transmission is mediated by blood-sucking triatomine bugs such as *Triatoma infestans* [11]. Moreover, blood transfusion and congenital transmission have been encountered, particularly, in humans [10]. These pathogens are all cyclically transmitted to mammalian hosts through the bite of haematophagus tsetse flies (*Glossina morsitans, Glossina palpalis*) [9] serving as vectors of the disease.

The consistent decimation of human populations and cattle by African trypanosomiasis has reached dramatic proportions and represents a social and economical obstacle for development [6,7]. In AAT, breeding animal losses are estimated to cost African farmers US$4.5 billion per year [8]. Bloodstream flagellated protozoan, members of the taxonomic genus *Trypanosoma*, are incriminated as the causative agents [1-7]. *Trypanosoma brucei rhodesiense* and *Trypanosoma brucei gambiense* provoke human African trypanosomiasis ("sleeping sickness") while *Trypanosoma congolense, Trypanosoma simiae, Trypanosoma vivax* and *Trypanosoma brucei brucei* cause animal African trypanosomiasis ("nagana") [http://www.vet.uga.edu/vpp/gray_book/FAD/AAT.htm].

In the particular case of human African trypanosomiasis, the trypanosomes multiply in the blood and lymph glands of the infected persons, therefore, defining the first-stage of sleeping sickness [5,13]. The symptoms in this early stage are characterized by bouts of fever, headaches, skin itching, pain in the joints, gradual loss of weight, nausea and vomiting [6,9]. Later, in the second stage, the trypanosomes cross the blood-brain barrier and invade the central nervous system to cause sleeping sickness. Sleeping sickness is characterized by neurological disorders such as mental confusion, sensory disturbances and poor muscular coordination, and reversal of the circadian sleep/wake cycle (insomnia in the night, drowsiness in the daytime) [5,9,13,14] hence, the nickname "sleeping sickness". In the absence of effective treatment, sleeping sickness invariably leads to death [3,6].

Control measures for African trypanosomiasis are directed either against the transmission vector through eradication of the tsetse fly, or against the causative pathogen, trypanosomes. Although vector control strategies had been effective in the past, they have been virtually abandoned because of their harmful effects on the environment [7]. Treatment of infected persons with the few available synthetic trypanocidal agents have shown significant drawbacks [15-17] related to high cost, host toxicity, limited oral bioavailability, and a requirement for hospitalization during the entire course of treatment. The emergence of drug resistance has also limited the choice and effectiveness of affordable agents in clinical use. Moreover, the type of treatment depends on the stage of the disease: hemolymphatic (first stage) or cerebral (second stage). Effectiveness in the second stage relies on the ability of the drug to cross the blood-brain barrier and reach concentrations high enough to kill the infective trypanosome. The four trypanocidal drugs, shown below [5,6,13] that have been clinically used up-to-date against sleeping sickness are, in chronological order—: Suramin (developed in 1921 against *T. b. rhodesiense* in the first-stage infection), Pentamidine (discovered in 1941 against first-stage *T. b. gambiense* infection), Melarsoprol (developed in 1949 against both human-infective *Trypanosoma* subspecies in cerebral infection), and Difluoromethyl ornithine (developed in 1981 as an alternative to Melarsoprol treatment failure in cerebral sleeping sickness). FIGS. 1*a* and *b* show the known trypanocidal drugs for early stage infection which are suramin and pentamidine, respectively. Suramin has no oral bioavailability and causes hemolysis and kidney disease. Pentamidine has no oral bioavailability, is an immunosuppressive and causes bleeding. FIGS. 1*c* and 1*d* show the known trypanocidal drugs for cerebral infection which are melarsoprol and difluoromethyl ornithine (DFMO), respectively. Melarsoprol has no oral bioavailability and causes tumors in the brain, blood in the urine and stomach pain. DFMO has no oral bioavailability and has a high susceptibility to resistance.

In the absence of prospective vaccine candidates for the disease, the limitations and drawbacks of these drugs emphasize the crucial need to develop new safe, effective and affordable drugs (trypanocides) against all forms of human and veterinary trypanosomiasis.

The Chinese plant *Artemesia annua* has been used to treat malaria for centuries. Research in the past three decades have uncovered artemisinin derivatives like artemisinin, dihydroartemisinin, artemether, artesunate that have played a critical role in the management of infectios caused by the multi-drug resistant malaria parasite, *Plasmodium falciparum*. Artemisinin has also been reported to be selectively active against cancer cells in vitro [39]. Utzinger et al. have demonstrated the use of artemisinin derivatives against tropical parasite species *Schistosoma*, responsible for schistosomiasis [40]. The effect of artemisinin and its derivatives on *Leishmania major*, another tropical parasite provoking leishmaniasis has also been reported [41]. However, the widespread use of this class of semi-synthetic artemisinin derivatives have been limited by the high cost of production, low bioavailability and long treatment regimens.

African, Asian and Amerindian societies have a rich tradition [17] in the use of plants for medical care. However, only few reports exist on the phytochemical treatment of sleeping sickness [17] and other kinetoplastid infections. Artemisinins have never before been used to treat human and veterinary trypanosomiasis. Until now, no experimental study has been carried out to establish the effectiveness of artemisinin or its derivatives on any *Trypanosoma* species.

The inventors are the first report on the trypanocidal potency of artemisinin and by extension, artemisinin-derived compounds, including artelinic acid.

Therefore, an object of the invention is to prepare a pharmaceutical composition containing artemisinin lead compounds from natural resources for the treatment of trypanosomiasis. Medicinal plants such as *Artemesia annua* have secondary metabolites of diverse molecular structures, physico-chemical properties, and pharmacological activities and offer an invaluable reservoir for new remedies.

Another object of the invention is to provide a cost effective treatment for kinetoplastid infections.

Another object of the present invention is to provide a method of treating humans and other mammals with kinetoplastid infections with artemisimin compounds such as artemisinin and artelinic acid.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

SUMMARY OF THE INVENTION

The invention relates to the treatment of kintoplastid infections by administering a pharmaceutical composition containing an extract from the plant *Artemisia annua*. The invention also relates to synthetic artemisinins that show improved efficacy in treating kinetoplastid infections. This invention also relates to a method of treating kintoplastid infections with artelinic acid and artemisinins.

The accompanying drawings show illustrative embodiments of the invention from which these and other of the objectives, novel features and advantages will be readily apparent.

BRIEF DESCRIPTION OF THE FIGURES

FIG. 5*a* is a photograph showing untreated *Leishmania major* amastigotes;
FIG. 5*b* is a photograph showing the effect of 1 μg/ml MeOH extract of *Artemisia annua* on *Leishmania major* amastigotes;
FIG. 5*c* is a photograph showing the effect of 10 μg/ml MeOH extract of *Artemisia annua* on *Leishmania major* amastigotes;
FIG. 5*d* is a photograph showing the effect of 100 μg/ml MeOH extract of *Artemisia annua* on *Leishmania major* amastigotes.

DETAILED DESCRIPTION

Figure 1A:
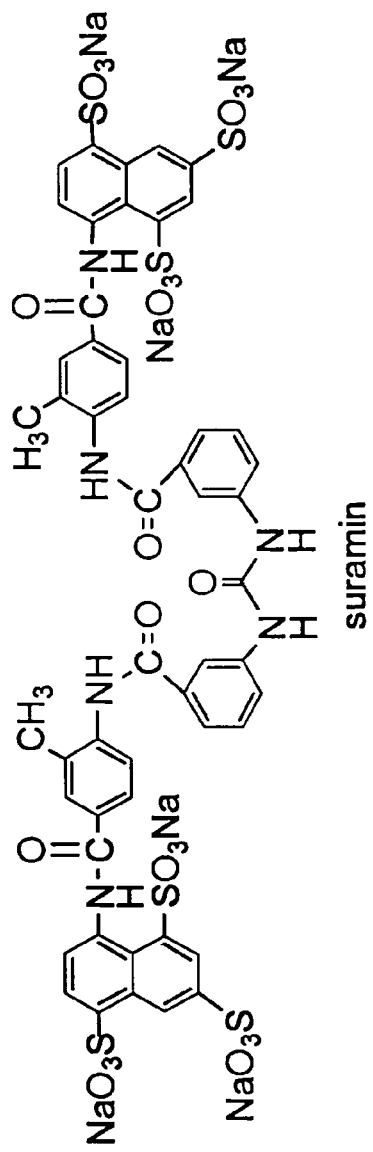
FIG. 1*a* is the chemical structure for suramin.
Figure 1B:
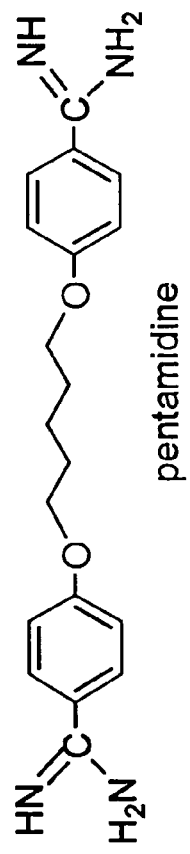
FIG. 1*b* is the chemical structure for pentamidine.
Figure 1C:
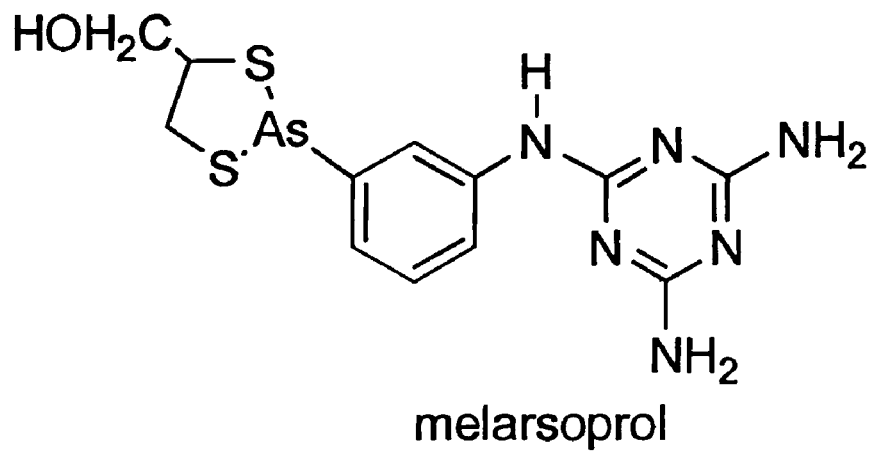
FIG. 1*c* is the chemical structure for melarsoprol.
Figure 1D:
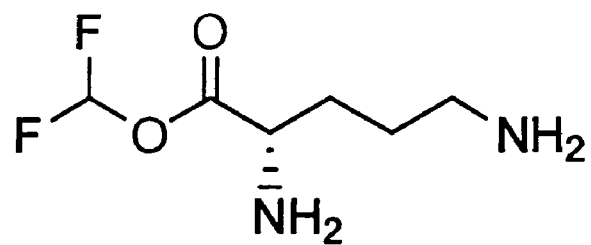
FIG. 1*d* is the chemical structure for difluoromethyl ornithine (DFMO.

The present invention relates to treatment of kinetoplasmid infections such as Leishmaniasis and Trypanosomaisis with artemisinins such as artelinic acid and/or trioxolane compounds.

The antimalarial activity of the artemisinins is believed to reside in the generation of toxic free oxygen radicals subsequent to the interaction with heme released from the metabolism of hemoglobin. The inventors have found that artemisinins and synthetic artemisinins, in particular, artelinic acid and trioxolane compounds, are effective in a method of treatment of kinetoplasmid infections, particularly against *Leishmania* and *Trypanosoma*.

The structural identity, and biological activity of compounds extracted from the medicinal plant *Artemesia annua* "Plant C-1 " was established. For these experiments, chromatographic techniques were used for total purification of the active principles. Various spectroscopic methods and conventional database analysis were also utilized for chemical structure elucidation. The identified candidates were subjected to standard bioassay protocols for in vitro characterization of their trypanocidal activity and also selective toxicity against trypanosomes versus mammalian host cells.

The extract of the plant *Artemesia annua* was shown to kill *Leishmania* parasited cultivated within mouse macrophages in vitro in a dose-dependant manner without significant toxicity to the mouse macrophages. The results were duplictated using commercially sourced artemisinin. The active compound in the compound was isolated and purified and chemically identified as artemisinin.

Materials and Methods a. Plant Material

*Artemesia annua* can be obtained in countries where it is cultivated such as its native China and Kenya. Freshly cut leaves of *Artemesia annua* were collected in Kenya, sun-dried and then ground into powder that can be stored in a refrigerator prior to extraction.

In the case of artemisinin, the compound was extracted from *Artemisia annua* with 70% aqueous EtOH at room temperature for 48 h (first extraction) and then 24 h each for the second and third extraction. The extracts were combined and concentrated under reduced pressure to obtain the EtOH extract. The EtOH extracts were purified by organic solvent fractionation and a combination of chromatographic procedures such as ion exchange on a DIAION HP-20 column and hydrophobic interaction on an ODS column and gel filtration on a Sephadex column. The active fractions were then identified. The following experiment confirms that the compounds that were extracted are efficacious against kinetoplastid infection and are artemisinins.

b. General Experimental Procedures: (Plant C-1)

$^1$H-NMR (500 MHz) spectra were measured on JEOL Lambda 500 spectrometer in $CHCl_3$-$d_1$ as well as MeOH-$d_4$ with TMS as an internal standard. $^{13}$C-NMR (600 MHz) and 2D-NMR (600 MHz) data were recorded on Varian Inova 600 in $CHCl_3$-$d_1$. Fast-atom bombardment (FAB) and high-resolution fast-atom bombardment (HR-FAB) mass spectra were recorded in positive ion mode JMS SX-102 spectrometer. For column chromatography, silica gel (Fuji Sylisia BW-200, Merck), ODS (Cosmosil 75$C_{18}$ OPN, Nacalai) were used. Thin-layer chromatography (TLC) analyses were performed over normal phase pre-coated plates (Kiesel gel 60$F_{254}$, Merck) and reversed-phase high-performance thin-layer chromatography (HPTLC) plates (RP-18 WF$_{254S}$, Merck). Spots on chromatograms were detected under UV light (254 and 365 nm) and by spraying with phosphomolybdic acid (5 g, EtOH 100 mL), vaniline/$H_2SO_4$ (vaniline 5 g, conc. $H_2SO_4$ 95 mL), and p-anisaldehyde/$H_2SO_4$ (AcOH 5 mL, conc. $H_2SO_4$ 25 mL, EtOH 425 mL, p-anisaldehyde 25 mL) followed by heating. For high-performance liquid chromatography (HPLC), detection of analytes was carried out with a refractive index detector (Shodex RI-71). For in vitro trypanocidal assay, stock solutions of samples were prepared in DMSO (Wako, for biochemical assay) which concentration in culture medium never exceeded 1%. Pentamidine (Sigma) was used as a positive control. For cytotoxic evaluation in vitro, mitomycin C was used as the positive control.

c. Trypanosome Stocks

Culture suspension of *Trypanosoma brucei brucei* (*T. b. brucei*) was obtained from Research Institute for Microbial Diseases (Osaka University, Japan). Trypanosomes were subcultured in appropriate medium (see 5.1.2) as frequently as needed to avoid overgrowth, and maintained in culture flasks at 37° C. in a humidified, 5% $CO_2$ atmosphere incubator. In addition, parasite culture stabilates were prepared by suspending trypanosomes centrifugation (1500 rpm, room temperature, 3 min) pellet in 1 mL of a mixture of 77% (v/v) trypanosome dilution buffer [56] and 33% (v/v) glycerol. The whole volume was transferred into cryotubes and stored at −80° C. until further needed.

d. Culture Medium for *Trypanosoma brucei brucei*

The axenic cultivation of the bloodstream forms of *T. b. brucei* was performed in Iscove's Modified Dulbecco's Medium (Gibco) supplemented with L-glutamine and 25 mM HEPES buffer. Additionally, 15% heat-inactivated (56° C., 40 min) fetal bovine serum (FBS, MultiSer) and also 0.05 mM bathocuproine disulfonic acid disodium salt (Dojin), 1.5 mM L-cystein (Nacalai), 1.0 mM hypoxanthine (Nacalai), 0.16 mM thymidine (TCI), 0.2 mM 2-mercaptoethanol (Sigma), and 1.0 mM sodium pyruvate (Nacalai) were aseptically incorporated in the culture medium.

e. Trypanocidal Assay

All fractions obtained stepwise in the course of the separation process of the plant crude extracts were assessed for their in vitro activity against *T. b. brucei*. Various concentrations of test samples were prepared in neat dimethyl sulfoxide (DMSO, Wako-for biochemical assay) then diluted in the culture medium so that DMSO content decreased to 10% in the medium. Trypanosomes were harvested at late exponential growth level, counted with a hemocytometer (Erma Tokyo 7059), and resuspended by appropriate dilution in culture medium for achieving a final density of $1\times10^4$ cells/mL. Aliquots of 90 µL of *T. b. brucei* suspension ($1\times10^4$ cells/mL) were transferred in wells of a Becton Dickinson 96-well microculture plate. Then, 10 µL of each sample preparation containing 10% DMSO were added to each inoculum well, achieving a final concentration of 1% DMSO. The microculture plate was incubated in a humidified, 5% $CO_2$ atmosphere incubator at 37° C. After successively 24, 48, and 72 hr-incubations, parasites viability was determined by observing directly inside the wells of the microculture plate with an optical microscope (Injectoscope model IMT-YF/Olympus). The in vitro trypanocidal potency of each sample was then evaluated and translated into mathematic symbols [(−): <80% growth inhibition level, (±): ≧80% growth inhibition level, (+): 100% growth inhibition level]. Control wells with the commercial drug pentamidine (positive control) and the solvent DMSO only (negative control) were also achieved in the same conditions as the test samples. A blank (parasites only in culture medium) was also included for reference.

f. Culture Medium for HeLa S3 Cells

An axenic culture of human carcinoma HeLa S3 cell line was established in Dulbecco's Modified Eagle's Medium (D-MEM, Sigma) supplemented with 4500 mg glucose/L, L-glutamine, $NaHCO_3$, and pyridoxine HCl, to which 10% heat-inactivated (56° C., 40 min) fetal bovine serum (FBS, MultiSer) was added.

g. Sample Preparation for Cytotoxic Evaluation In Vitro

Plant chromatographic fractions, which have shown potent trypanocidal activity in vitro, were selected for cytotoxicity assay. Previously dissolved in neat DMSO (Wako-for biochemical assay), an aliquot of 10 µL of each test sample was diluted in 490 µL of the cell culture medium with the intent of decreasing the DMSO concentration to 2% in the medium.

h. Cytotoxicity Assay In Vitro

HeLa S3 cells maintained in culture dish (Sumilon) were washed with Dulbecco's phosphate saline buffer (−) [DPBS (−), Nissui Pharmaceutical Co., Ltd] after syphonating the culture medium. Adherent cells were released from their dish bottom substrate by adding trypsin (Nacalai) and gently tapping with hand on the round lateral side of the dish. Thus, trypsinized cells were harvested, suspended in culture medium then centrifuged at 800~1000 rpm for 3 min at room temperature. After removing the supernatant, the remaining pellet was resuspended in the culture medium. Cells were counted with a hemocytometer (Erma Tokyo 7059), and then diluted appropriately to achieve a final density of $1\times10^5$ cells/mL in the culture medium. Later on, cells were seeded in a 96-well microtiter plate (Becton Dickinson), each well containing 100 µL ($1\times10^5$ cells/mL) of cell suspension. Then, 100 µL of test samples preparation (see 5.2.2) were added in triplicate for each concentration into respective wells, thus achieving a final concentration of 1% DMSO. Respective triplicate wells for the positive control (mitomycin C) and the negative control (1% DMSO only in culture medium) were also included. After 72 hr-incubation at 37° C. in a humidified, 5% $CO_2$ atmosphere incubator (Sanyo), 25 µL of MTT [3-(4,5-dimethylthazol-2-yl)-2,5-diphenyl tetrazolium bromide] [57-59] reagent were added to each well including controls. The microtiter plate was returned in the same incubator for an additional 3 hr-exposure at 37° C. to allow the formazan [57-59] crystals to accumulate. Then, supernatants were syphonated from the wells and 200 μL of DMSO were added to solubilize the formazan crystals. After shaking (MS1 Minishaker IKA) for 3-5 min, the absorbance in each well was measured at 540 nm in a microtiter plate reader (ImmunoMini NJ-2300). The percentage of cytotoxicity (growth inhibition level) was calculated as (A-B)/A×100, where A is the mean optical density of negative control wells and B is the mean optical density of test sample wells.

i. Bioassay-guided Isolation of Active Constituents of Artemisinin

Dried and pulverized powder from "plant C-1" (2.3 kg) were extracted three times with 80% ethanol after 24-hr maceration (first time) and 3-hr maceration (second and third time) at room temperature. The liquid extracts were combined, filtered, and concentrated under reduced pressure with a rotary evaporator below 30° C. The ethanolic residue (240 g) obtained exhibited a complete inhibition of trypanosomes growth at 30 μg/mL after 24-hr exposure and 100% growth inhibition in vitro against $T.\ b.\ brucei$ at 100 μg/mL after 24-hr exposure. This residue was later on dissolved in double-distilled water, then subjected to solvent-solvent partition in EtOAc and n-BuOH to yield, after solvent evaporation, 72 g of EtOAc extract, 74 g of n-BuOH extract, and 94 g of $H_2O$ extract. The strongest trypanocidal activity in vitro was observed in the EtOAc extract exhibiting 100% and ≧80% growth inhibition against $T.\ b.\ brucei$, respectively, at the concentrations of 50 μg/mL and 5 μg/mL after 24 hr-exposure. This most potent EtOAc residue was applied to $SiO_2$ gel column and eluted successively with binary solvent mixtures of hexane: EtOAc=4:1→1:1→1:1.5→1:2→100% MeOH. The eluted fractions were monitored by normal phase TLC and similar fractions were pooled into five main fractions named A (280 mg), B (341 mg), C (1.72 g), D (1.84 g), and E (690 mg). Among them, fraction C was the only one that showed trypanocidal activity until the low concentration value of 1 μg/mL, thus featuring ≧80% growth inhibition after 24-hr incubation. Further separation of fraction C carried out by reversed-phase ODS column chromatography and eluting gradually with 60% MeOH→80% MeOH→90% MeOH→100% MeOH yielded seven fractions named from C-1 to C-7. Fractions C-4 (629 mg), C-5 (16 mg), and C-6 (139 mg) showed the highest biological potency and an encouraging selectivity toward HeLa cell in vitro at 0.5 μg/mL with, respectively, 100% trypanocidal level and 5.5% cytotoxic level for C-4, ≧80% trypanocidal level and 10.5% cytotoxic level for C-5, and ≧80% trypanocidal level and 14.9% cytotoxic level for C-6.

Figure 2:
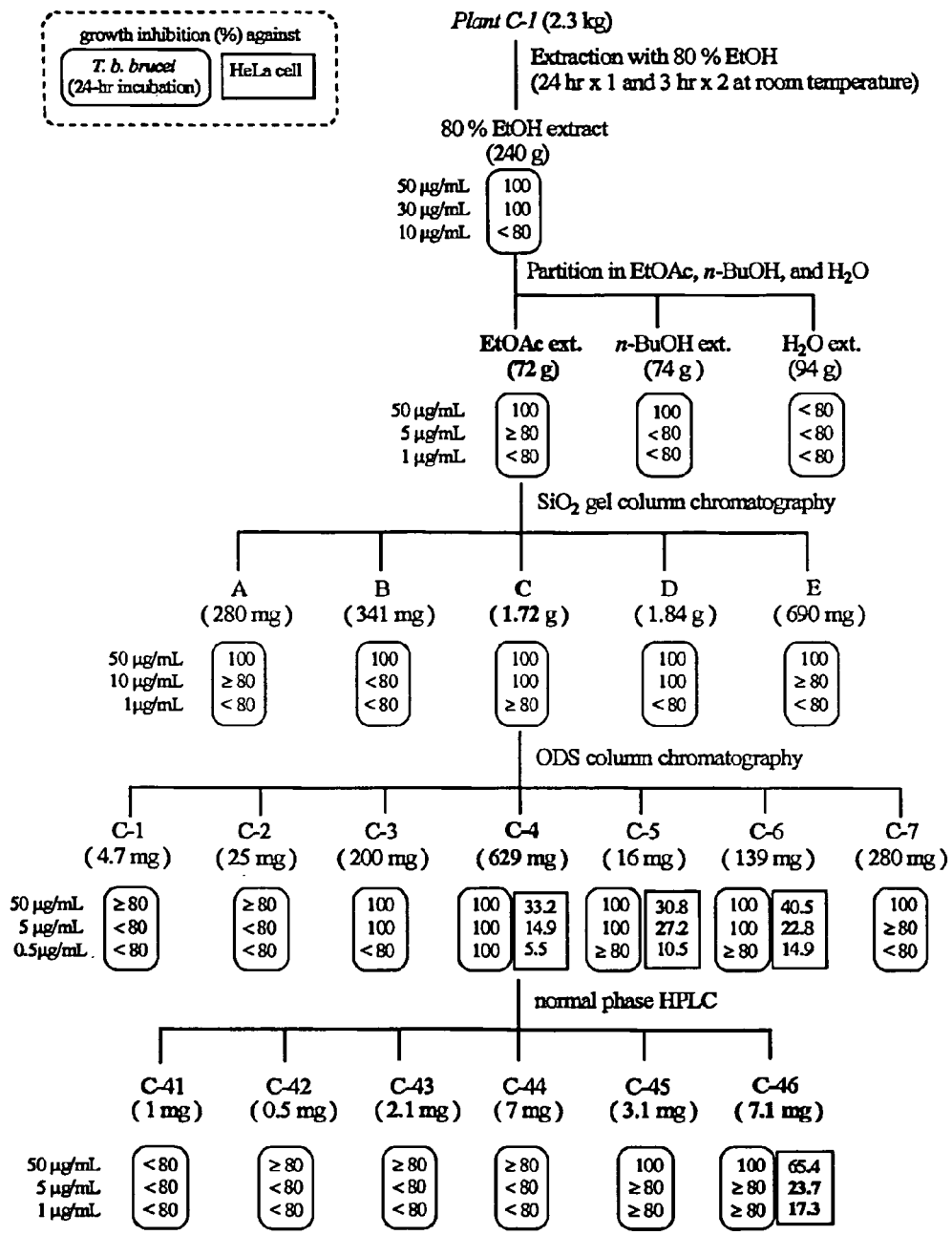
FIG. 2 is a Flow diagram showing the bioassay-guided isolation of active constituents of plant C-1 leading to C-46.
Figure 3:
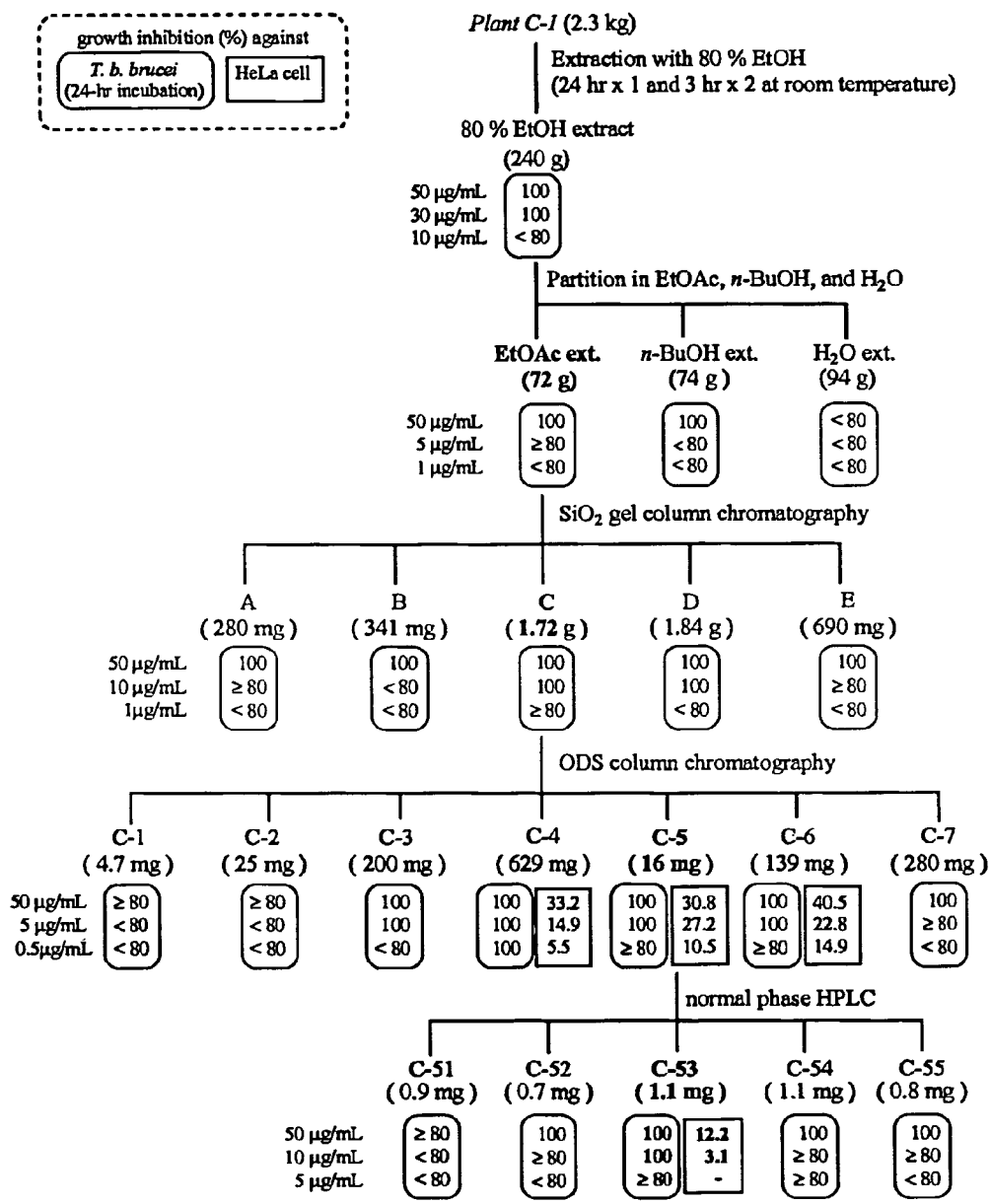
FIG. 3 is a flow diagram showing the bioassay-guided isolation of active constituents of plant C-1 leading to C-53.

Firstly, C-4 was subjected to final purification with HPLC (column: 5 SL-II type Waters, 10×250 mm i.d.; flow rate: 3.0 mL/min; detection: refractive index detector at range 512; eluent: hexane/EtOAC=8/1) leading to isolation of C-46 (7.1 mg) at a $t_R$ of 21.27 min (FIG. 2), whose trypanocidal activity in vitro was ≧80% growth inhibition after 24-hr incubation and the cytotoxic level in vitro was 17.3% at 1 μg/mL. Secondly, C-5 was purified by normal phase HPLC (column: 5 SL-II type Waters, 10×250 mm i.d.; flow rate: 3.0 mL/min; detection: refractive index detector at range 512; eluent: hexane/EtOAC=7/1) affording C-53 (1.1 mg) at $t_R$=12.99 min (FIG. 3). Because of the small amount yielded by C-53, extensive spectral data measurement was inconvenient. Only $^1$H-NMR data could be obtained. Thus, purification was repeated starting off with a larger quantity of EtOAc extract. Fortunately, 11.0 mg of C-53 were obtained. According to the bioassay outcome, C-53 showed ≧80% growth inhibition in vitro against $T.\ b.\ brucei$ after 24-hr incubation at 1 μg/mL, and only 3.1% inhibition ratio against HeLa cells in vitro at 5 μg/mL.

j. Chemical Structure of C-46

Figure 4A:
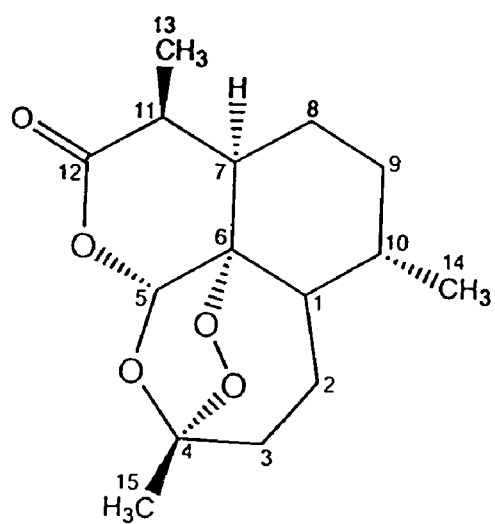
FIG. 4*a* is the chemical structure of artemisinin C-46.
Figure 4B:
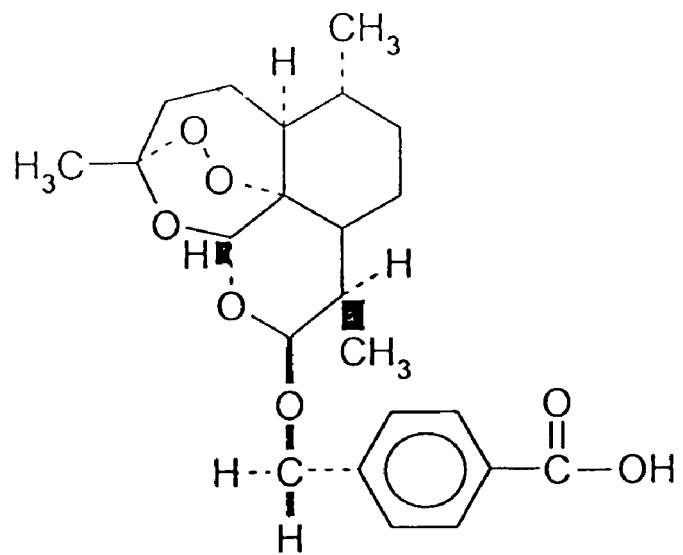
FIG. 4*b* is the chemical structure of Artelinic acid.
Figures 6, 7:
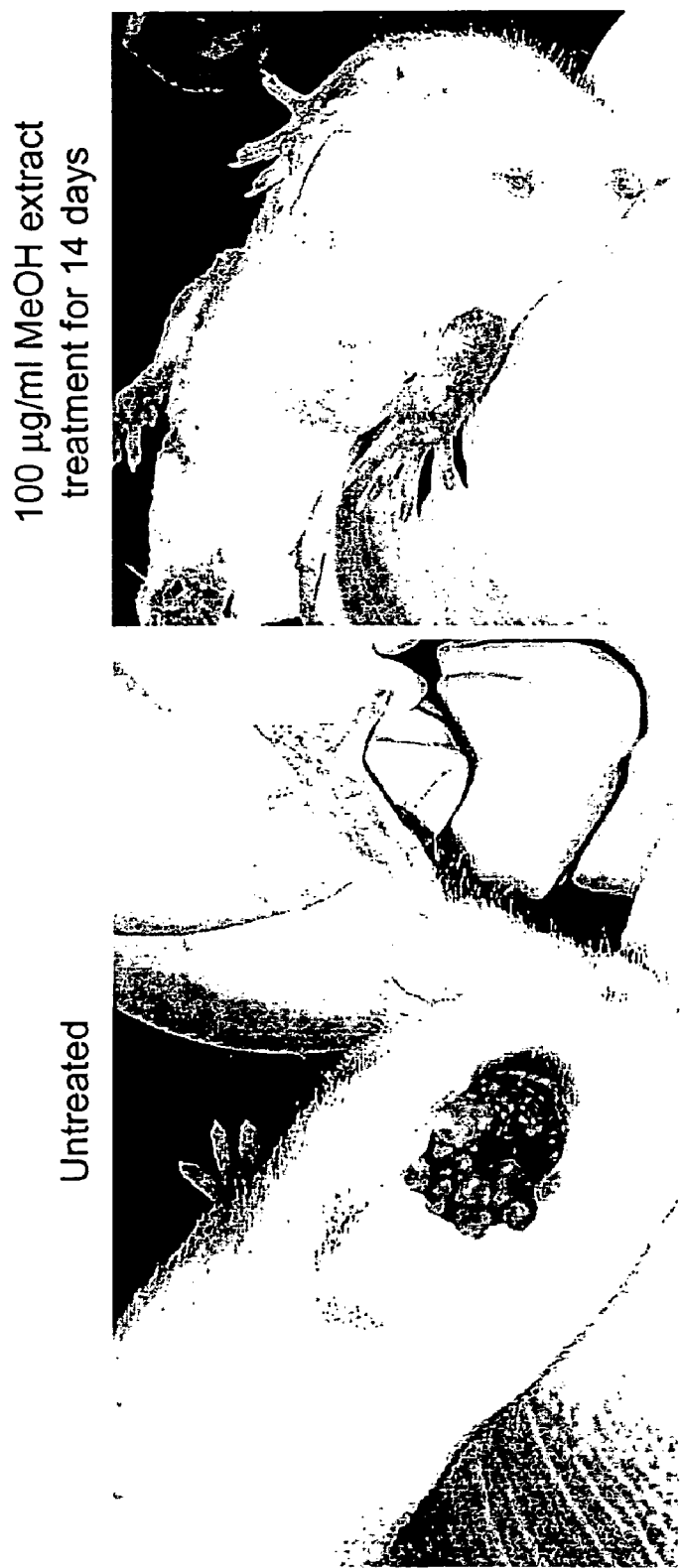
FIG. 6 is a photograph showing the foot of an untreated mouse.
FIG. 7 is a photograph showing a mouse foot with the effect of 100 μg/ml MeOH extract treatment for 14 days.

Comparison of $^1$H- and $^{13}$C-NMR, $^1$H-$^1$H COSY, HMBC, FAB-MS, and specific rotation data in our hands with those reported in the literature [34,35] led to conclusion that C-46 was (+)-artemisinin (FIG. 4).

$^1$H-NMR spectrum analysis for structure elucidation of C-46 indicated the presence of doublet peaks, respectively, at δ1.19 (3H, d, J=7.4 Hz) and δ0.98 (3H, d, J=6.0 Hz), and a singlet peak at δ1.43 (3H, s). This set of peaks was indicative of the three methyl groups at C-13, C-14, and C-15, respectively. The signal observed at δ5.84 was assignable to H-5, which corresponding carbon signal was displayed at δ93.9 on the $^{13}$C-NMR spectrum. The signal that appeared at δ172.2 was assignable to the carbonyl moiety of the lactone group at C-12. The signal that appeared at δ105.6 was due to the quartenary carbon C-4 activated by two geminal oxygen atoms. The peak observed at δ79.7 was due to the quartenary carbon C-6 connected to an oxygen atom. In addition, the positive ion mode FAB-MS displayed $[M+Li]^+$ at m/z 289 (65%), $[M+Na]^+$ at m/z 305 (100%), and $[M+H]^+$ at m/z 283 (12%). Additionally, the optical rotation parameter revealed $[\alpha]_D^{24}$=+41.5 (c=0.2, $CHCl_3$). Comparison between spectral data in our hands with those in the literature database led to conclusion that C-46 corresponded to (+)-artemisinin ($C_{15}H_{22}O_5$, Mw=282).

k. Chemical Structure of C-53

Relevant $^1$H— and $^{13}$C-NMR, $^1$H-$^1$H COSY, HMQC, HMBC, NOESY, FAB-MS, and HRFAB-MS data were recorded; the specific rotation value was calculated.

C-53 has trypanocidal potency in vitro but is slightly weaker than that of (+)-artemisinin. Nevertheless, from its chemical characterization, 1 D- and 2D-NMR, FAB- and HRFAB-MS, and specific rotation data that have been collected, spectral data analysis reveals that C-53 might be polyalicyclic; containing three characteristic methyl substituents and an unsaturated lactone ring; displaying a molecular weight of 234 associated to the chemical formula $C_{15}H_{22}O_2$. Accordingly, C-53 is presumed to be a sesquiterpene lactone congenere of artemisinin, but obviously lacking the endoperoxide bridge. This activity is of more general interest because the mechanism of action of artemisinins, as an anti-plasmodial or anti-tumoricidal agent, is believed by some to be related to the presence of the endoperoxide bridge.

The information obtained by careful examination of C-53 and C46 as well as other eluted compounds in the above experiment verify that artemisinins are active ingredients in artemeseia annua that hinder the growth of kintoplastid infections.

Both compounds Artemisinin and Artelinic acid belong to the same class of compounds and both have been found by the inventors in testing to be effective against leishmaniasis and other kinteplastid infections.

EXAMPLE 1

Preliminary drug screening (in vitro amastigote/macrophage culture) of artemisinin and artelinic acid compounds.

Four compounds were obtained.
BN: 97471 artelinic acid
ZW: 60909 dihydroartemisinin
BN: BL 48816 WR# 255131 (Beta-Arteether)
BN: BL 50129 WR#: 249309 (Artemisinin QHS)

The four compounds were dissolved in the respective solvents as indicated in the table below (Table 1) and were tested against *Leishmania major* ATCC 50122 amastigotes in vitro in a mouse macrophage system. A positive (Pentostam) and negative (culture medium) controls were set for each plate. Compounds were tested at 2.0 µM in a total volume of 2-0 mls. Drug was added to well every 4 hours×1, 2 and 3, and results shown in (Table 2) below.

TABLE 1

| Compound. | Solvent. | Conc. Used. | Volume. |
|---|---|---|---|
| 1 Artelinic acid | Methanol. | 2.0 µM | 5.6 µl/2 ml. |
| 3 Dihydro artemisinin | DMSO. | 2.0 µM | 1.1 µl/2 ml |
| 5 B-Arteether | DMSO | 2.0 µM | 1.18 µl/2 ml |
| 6 Artemisinin | Methanol. | 2.0 µM | 1.2 µl/2 ml |

Results

TABLE 2

| Compound | Compound added q4 h ×1 | Compound added q4 h × 2 | Compound added q4 h × 3 |
|---|---|---|---|
| Artelinic Acid 1 | No intracellular amastigote was seen in the ctoplasm of the macrophages. Cytoplasm stained pinkish instead of purplish which is an indication of cell cytotoxicity. | No amastigote was seen in the macrophages. Apart from staining pinkish, the cells cytoplasm looked mushy and seem to desentegrate. | same |
| Dihydro artemisinin 3 | About 50% of macrophages had intracellular *leishmania* amastigotes. Cells morphology was normal. | About 30% of macrophages had intracellular *leishmania* amastigotes. Cells morphology was normal. | About 5-7% of macrophages had intracellular *leishmania* amastigotes. About 30% of macrophages had intracellular *leishmania* amastigotes |
| B Arteether | About 90% of macrophages had *leishmania* amastigotes similar to the Negative control Cytoplasm stained poorly (pinkish). | About 90% of macrophages had *leishmania* amastigotes similar to the Negative control Cytoplasm stained poorly (pinkish). | About 50% of macrophages had *leishmania* amastigotes similar to the Negative control Cytoplasm stained poorly (pinkish) with mild cytotoxicity. |
| 6 Artemisinin | No difference between control and the macrophages subjected to the test compound. About 80% of the cell had between 4-7 parasites per macrophage. Cell morphology was normal. | same | same |

The results of the initial screen showed that Artelinic acid at 2 uM cleared all of the amastigates in macrophages. Observer also noted pinkish staining of the cytoplasm of the macrophages that was interpreted as cell toxicity. However, similar changes were also noted in the negative control that had no compound added. The effectiveness of the WRAIR compounds tested in the screen was judged to be:

Artelinic acid>>>Dihydroartemisinin>Beta Arteether>>Artemisinin.

Because of the high potency of Artelinic acid relative to the other compounds, the experiments were repeated with different doses of Artelinic acid alone. Additionally, the addition of drug to culture wells q4h did not seem to affect the results for this compound (Table 2). Hence, Artelinic acid was added once in the dose response experiments (Table 3).

The initial observation implicating Artemisinins was obtained with crude extracts from the plant (*Artemesia annua*. On the strength of these results Artemisinin-derived compounds that had been synthesized previously as potential anti-malarials were secured from the WRAIR inventory and tested (See U.S. Pat. No. 4,791,135, incorporated in its entirety by reference for the preparation of synthetic artemisinins, dihydroartemisinins, and artesunic acid.). The active principle in the plant extract was prepared into pharmaceutical compositions suitable for treating kinetoplastid infections.

Pharmaceutical compositions containing the active ingredients from the plant *artemesia annua*, including artemisinins and artelinic acid can be prepared using any known pharmaceutical carrier suitable for i.p. injection including but not limited to saline. Carriers for oral administration can be capsules or pills made by any known and accepted pharmaceutical composition used for carrying active ingredients to the digestive tract. Acceptable doses for oral administration are 4-8 ul/kg for i.p or oral administration. Concentrations for in vitro testing are 0.01 to 2.0 uM Effects of Different Concentrations of Artelinic Acid (Dose Response) on *Leishmania* Amastigotes.

selected and treated daily with test article for one week. The first doses were administered on 18 May. Lesions were measured with calipers prior to dosing and 9 days after commencement of treatment (27 May) and the difference in lesion size calculated. The thickness of the uninfected footpad was also measured. Only Artelinic acid and the crude methanol extract of the plant *Artemesia annua*, that had shown marked potency in the mouse macrophage/amastigote in vitro screen were tested in vivo. Test articles were administered orally and intra-peritoneally (ip).

TABLE 3

| Concentration. | Observation Results. |
| --- | --- |
| 2.0 µM | All the *leishmania* amastigotes were cleared but the cell showed some marked pink staining. |
| 1.0 µM | All the amastigotes were cleared from the macrophages and some vacuoles could be seen in the macrophage cytoplasm. Mild cell pink staining was noticed. |
| 0.5 µM | Cleared all the parasites in the cytoplasm. Some cells showed pinkish staining. |
| 0.25 µM | Cleared all the *Leishmania* amastigotes and no noticeable pink staining of cells. The cell morphology was normal as compared to the control cells. |
| 0.1 µM | There was reduction of intracellular *Leishmania* amastigotes in the macrophages but unable to clear them completely. No pinkish stain of cells was noticed. |
| 0.05 µM | No effect of the drug was seen on either the *Leishmania* parasites or the macrophages. |
| Control. | 90% of the macrophages were infected with between 5-7 parasites per cell. |

As shown in the results above (Table 3), killing of intracellular amastigotes was noted at concentrations as low as 0.1 µM of Artelinic acid and clearance was complete at doses as low as 0.25 µM of compound.

EXAMPLE 2

In Vivo Testing in BALB/c Mice

Because of the marked potency of Artelinic acid in the clearance of intracellular *Leishmania* amastigotes, an in vivo screen was undertaken using BALB/C mice. One foot pad was infected with infective *Leishmania* promastigotes while the other foot served as control. After the infected foot pads had developed lesions, mice with similar size lesions were

TABLE 4

| Compound | Dose | Admin Route | Footpad Thickness (mm) Uninfected Foot | Lesion Size (mm) Pre-Rx | Lesion Size (mm) Post-Rx | Diff Lesion size (mm)* |
| --- | --- | --- | --- | --- | --- | --- |
| Artelinic acid | 4 ul/Kg | Oral | 1.5 | 2.8 | 2.0 | −0.8 |
| | | Oral | 1.5 | 2.7 | 2.0 | −0.7 |
| | | Oral | 1.5 | 2.8 | Ulcerated | |
| | | IP | 1.5 | 2.6 | 2.1 | −0.5 |
| | | IP | 1.5 | 2.5 | 2.2 | −0.3 |
| | | IP | 1.6 | 2.6 | 2.0 | −0.6 |
| Plant extract | 8 ul/Kg | Oral | 1.2 | 2.9 | 2.0 | −0.9 |
| | | Oral | 1.3 | 2.8 | 2.0 | −0.8 |
| | | IP | 1.4 | 2.7 | 2.2 | −0.5 |

TABLE 4-continued

| Compound | Dose | Admin Route | Footpad Thickness (mm) Uninfected Foot | Lesion Size (mm) Pre-Rx | Lesion Size (mm) Post-Rx | Diff Lesion size (mm)* |
|---|---|---|---|---|---|---|
| | | IP | 1.5 | 2.8 | 1.8 | −1.0 |
| | | IP | 1.5 | 2.6 | 2.7 | +0.1 |
| Pentostam | 20 mg/Kg | Oral | 1.4 | 2.8 | 2.6 | −0.2 |
| | | Oral | 1.5 | 2.7 | 2.9 | −0.2 |
| | | Oral | 1.5 | 2.7 | 2.9 | +0.2 |
| | | IP | 1.6 | 2.8 | 2.3 | −0.5 |
| | | IP | 1.5 | 2.8 | 3.0 | +0.2 |
| | | IP | 1.6 | 2.6 | 2.7 | +0.1 |
| Control | N/A | | 1.4 | 2.5 | 2.8 | +0.3 |

*(positive value indicates worsening and a negative value healing of the lesion with time)

Results (Table 4) show that Artelinic acid and plant extract of *Artemesia annua*, containing artemisinins, either given orally or ip to BALB/c mice for one week led to a decrease in the size of *Leishmania major* lesions induced in the footpad of the animals. Both Artelinic acid and plant extract were much more effective than Pentostam, the positive control, at the doses and route of administration tested.

The in vivo experiments, are remarkable in that Artelinic acid and the active ingredient in the plant extract, artemisinins, show potency against *Leishmania* when administered orally. Moreover the in vitro experiments demonstrate that these compounds do not require to be metabolized into an active moiety by the liver for them to show potency against intracellular *Leishmania* amastigotes.

The invention has been described herein with reference to certain preferred embodiments. However, as obvious variations thereon will become apparent to those skilled in the art, the invention is not to be considered as limited thereto.

REFERENCES

1. Dobson, R. Sleeping sickness re-emerges in Africa after years of civil war. *British Medical Journal*, 2005, 322: 1382.
2. Chretien, J. P.; Smoak, B. L. African trypanosomiasis: changing epidemiology and consequences. *Current Infectious Disease Reports*, 2005, 7: 54-60.
3. Stich, A.; Abel, P. M.; Krishna, S. Human African trypanosomiasis. *British Medical Journal*, 2002, 325: 203-206.
4. World Health Organization. Pan African tsetse and trypanosomiasis eradication campaign. Provisional agenda item 13.17 of the Fifty-fifth World Health Assembly, 30 Apr. 2002, Secretariat Report A55/22, WHO, 2002.
5. Gull, K. The cell biology of parasitism in *Trypanosoma brucei*: insights and drug targets from genomic approaches? *Current Pharmaceutical Design*, 2002, 8: 241-256.
6. World Health Organization. African trypanosomiasis or sleeping sickness. Fact Sheet N-259, WHO, 2001.
7. Grant, I. F. Insecticides for tsetse and trypanosomiasis control: is the environmental risk acceptable? *Trends in Parasitology*, 2001, 17(1): 10-14.
8. Butler, D. African labs win major role in tsetse-fly genome project. *Nature*, 2004, 427(6973): 384.
9. Bisoffi, Z.; et al. African trypanosomiasis Gambiense, Italy. *Emerging Infectious Diseases*, 2005, 11(11): 1745-1747.
10. Morel, C. M.; Lazdins, J. Chagas disease. *Nature Reviews Microbiology*, 2003, 11: 14-15.
11. Panzera, F.; et al. Genomic changes of Chagas disease vector, South America. *Emerging Infectious Diseases*, 2004, 10(3): 438-446.
12. El-Sayed, N. M.; et al. The genome sequence of *Trypanosoma cruzi*, etiologic agent of Chagas disease. *Science*, 2005, 309: 409-410.
13. Kennedy, P. G. E. Human African trypanosomiasis of the CNS: current issues and challenges. *The Journal of Clinical Investigation*, 2004, 113: 496-504.
14. Legros, D. Treatment of human African trypanosomiasis-present situation and needs for research and development. *The Lancet Infectious diseases*, 2002, 2: 437-440.
15. Freiburghaus, F.; Steck, A.; Pfander, H.; Brun, R. Bioassay-guided isolation of a diastereoisomer of kolavenol from Entada abyssinica active on *Trypanosoma brucei rhodesiense*. *Journal of Ethnopharmacology*, 1998, 61: 179-183.
16. Camacho, M. del R.; et al. In vitro activity of *Triclisia patens* and some bisbenzylisoquinoline alkaloids against *Leishmania donovani* and *Trypanosoma brucei brucei*. *Phytotherapy Research*, 2002, 16: 432-436.
17. Freiburghaus, F.; Kaminsky, R.; Nkunya, M. H. H.; Brun, R. Evaluation of African medicinal plants for their in vitro trypanocidal activity. *Journal of Ethnopharmacology*, 1996, 55: 1-11.
18. El-Sayed, N. M.; et al. Comparative genomics of Trypanosomatid parasitic protozoa. *Science*, 2005, 309: 404-408.
19. Rawlings, N. D.; Tolle, D. P.; Barrett, A. J. MEROPS: the peptidase database. *Nucleic Acids Research*, 2004, 32: D160-D164.
20. Gibson, W. Species concepts for trypanosomes: from morphological to molecular definitions? *Kinetoplastid Biology and Disease*, 2003, 2: 10-15.
21. Despommier; Gwadz; Hotez; Knirsch. Parasitic Diseases, 5$^{th}$ Edition, Apple Trees Productions, L.L.C. NY, p. 34.
22. Seed, J. R.; Wenck, M. A. Role of the long slender to short stumpy transition in the life cycle of the African trypanosomes. *Kinetoplastid Biology and Disease*, 2003, 2: 3-10.
23. Klayman, D. L.; et al. Isolation of artemisinin (Qinghaosu) from *Artemisia annua* growing in the United States. *Journal of Natural Products*, 1984, 47 (4): 715-717.
24. Yadav, J. S.; Babu, R. S.; Sabitha, G. Stereoselective total synthesis of (+)-artemisinin. *Tetrahedron Letters*, 2003, 44: 387-389.
25. Lai, H.; Singh, N. P. Oral artemisinin prevents and delays the development of 7,12-dimethylbenz[a]anthracene (DMBA)-induced breast cancer in the rat. *Cancer Letters*, 2006, 231: 43-48.

26. Utzinger, J.; et al. Comparative study of the effects of artemether and artesunate on juvenile and adult *Schistosoma mansoni* in experimentally infected mice. *Transactions of the Royal Society of Tropical Medicine and Hygiene*, 2002, 96: 318-323.
27. Yang, D. M.; Liew, F. Y. Effects of qinghaosu (artemisinin) and its derivatives on experimental cutaneous leishmaniasis. *Parasitology*, 1993, 106 (Pt 1): 7-11.
28. Hammarton, T. C.; et al. The *Trypanosoma brucei* cyclin, CYC2, is required for cell cycle progression through $G_1$ phase and for maintenance of procyclic form cell morphology. *The Journal of Biological Chemistry*, 2004, 279 (23): 24757-24764.
29. Carmichael, J.; et al. Evaluation of a tetrazolium-based semiautomated calorimetric assay: assessment of chemosensitivity testing. *Cancer Research*, 1987, 47 (4): 936-942.
30. Carmichael, J.; et al. Evaluation of a tetrazolium-based semiautomated calorimetric assay: assessment of radiosensitivity. *Cancer Research*, 1987, 47 (4): 943-946.
31. Ueng, T.-H.; et al. Induction of fibroblast growth factor-9 and interleukin-1α gene expression by motorcycle exhaust particulate extracts and benzo(a)pyrene in human lung adenocarcinoma cells. *Toxicological Sciences*, 2005, 87 (2): 483-496.

What is claimed is:

1. A method of treating kinetoplastid infections in a mammal comprising: orally administering synthetic artelinic acid to said mammal until said kinetoplastid infection is reduced or cured.

2. A method of treating a kinetoplastid infection in a mammal, comprising orally administering an effective amount of a pharmaceutical dosage form of artelinic acid to said mammal.

3. The method of claim 2, wherein said kinetoplastid infection is intracellular *Leishmania* amastigotes.

4. The method of claim 1, wherein said artelinic acid is administered in a dose of 4-8 ul/Kg.

5. The method of claim 2, wherein said artelinic acid is administered in a dose is of 4-8 ul/Kg.

6. The method of claim 1, wherein said synthetic artelinic acid is water soluble.

* * * * *